United States Patent
Werner et al.

(10) Patent No.: US 7,468,519 B2
(45) Date of Patent: Dec. 23, 2008

(54) NEAR INFRARED LIGHT DIFFUSER

(75) Inventors: Gregory J. Werner, Puyallup, WA (US); Paul H. Shelley, Lakewood, WA (US)

(73) Assignee: The Boeing Company, Chicago, IL (US)

( * ) Notice: Subject to any disclaimer, the term of this patent is extended or adjusted under 35 U.S.C. 154(b) by 4 days.

(21) Appl. No.: 11/566,902

(22) Filed: Dec. 5, 2006

(65) Prior Publication Data
US 2008/0129995 A1   Jun. 5, 2008

(51) Int. Cl.
*G01J 5/54* (2006.01)

(52) U.S. Cl. ................................. 250/458.1

(58) Field of Classification Search .............. 250/341.6, 250/341.8, 340, 341.1, 341.2, 341.5; 359/599, 359/707
See application file for complete search history.

(56) References Cited

U.S. PATENT DOCUMENTS

| | | | | |
|---|---|---|---|---|
| 3,693,025 A | | 9/1972 | Brunton | |
| 4,129,781 A | * | 12/1978 | Doyle | 250/341.3 |
| 5,241,366 A | * | 8/1993 | Bevis et al. | 356/632 |
| 5,596,450 A | * | 1/1997 | Hannon et al. | 359/599 |
| 5,754,294 A | * | 5/1998 | Jones et al. | 356/503 |
| 5,781,342 A | * | 7/1998 | Hannon et al. | 359/599 |
| 5,838,406 A | * | 11/1998 | McGregor et al. | 349/113 |
| 5,892,621 A | * | 4/1999 | McGregor et al. | 359/599 |
| 5,905,594 A | * | 5/1999 | McGregor et al. | 359/599 |
| 5,982,542 A | * | 11/1999 | Hannon et al. | 359/559 |
| 6,015,610 A | * | 1/2000 | Minor et al. | 428/315.7 |
| 6,078,042 A | * | 6/2000 | Fellows | 250/252.1 |
| 7,223,977 B2 | * | 5/2007 | Shelley et al. | 250/339.01 |
| 2005/0136200 A1 | * | 6/2005 | Durell et al. | 428/35.7 |
| 2005/0263704 A1 | * | 12/2005 | Shelley et al. | 250/339.01 |
| 2007/0038041 A1 | * | 2/2007 | Yang et al. | 600/310 |
| 2008/0084609 A1 | * | 4/2008 | Lin | 359/599 |
| 2008/0149164 A1 | * | 6/2008 | Goedmakers et al. | 136/247 |

FOREIGN PATENT DOCUMENTS

| | | |
|---|---|---|
| DE | 102005025848 B3 | 2/2007 |
| WO | 2005077135 A2 | 8/2005 |

* cited by examiner

*Primary Examiner*—David P Porta
*Assistant Examiner*—David S Baker
(74) *Attorney, Agent, or Firm*—McNees Wallace & Nurick, LLC

(57) ABSTRACT

A system and method for measuring coating thickness upon a substrate is disclosed. A near infrared light is directed upon the coating and reflected near infrated light is collected to determine the coating thickness. A diffuser is placed between the coating and the reflected near infrared light collector to improve the accuracy of the measurement, especially for coating thickness of less than about 2 mils and for coatings with shiny surfaces. The diffuser is formed of a low density polytetrafluoroethylene fluoropolymer film.

16 Claims, 2 Drawing Sheets

NEAR INFRARED LIGHT DIFFUSER

FIELD OF THE INVENTION

The present invention is directed to measuring a coating thickness using a near IR absorbance technique and a diffuser for reducing specular interference.

BACKGROUND OF THE INVENTION

Surfaces of many different materials are coated in a variety of applications for aesthetic reasons and for protecting the surface against physical and environmental damage. It is desirable to determine the thickness of the coating applied to the surface for a number of reasons. It is also desirable to obtain as accurate a determination of thickness as possible, which, in the past, has been difficult for extremely thin coatings For example, it may be desirable to apply a minimum, predetermined thickness of a coating, such as a paint or primer material on a surface, since optimal adhesion of the paint coating is generally a function of the paint thickness. The paint or primer may be opaque. In addition, applying at least a minimum thickness of paint or primer to a surface ensures that any underlying visual features on the surface do not appear through the coating. This may be important in instances where projecting a professional image to customers is important, and to instill a feeling of customer confidence, such as through company signage or commercial airline tail art. This is also important for ensuring that a product, such as a motor vehicle or an airplane, displays a finish quality that is favored by the customer.

Further, applying at least a minimum thickness of the paint or primer may also provide a desired amount of protection from corrosion, or other deterioration of the underlying surface and substrate. For example, many surfaces that are painted are subject to environments that are conducive to corrosion, such a marine vessels that operate in water, which may include salt water. Further, motor vehicles and airplanes often operate in rainy or humid environments. Therefore, it is desirable to provide at least a minimum amount of protection against the corrosive effects of these environments.

In some applications, weight is an important consideration. For example, it is desirable to minimize weight of an airplane to reduce fuel consumption. Since the exterior surface area of the airplane may be significantly large, a paint and primer applied t the exterior surface can be a significant factor in the total weight of the airplane. Therefore, it may also be desired in some applications to limit thickness of paint or primer coating on a surface to a predetermined maximum thickness.

In order to ensure that a minimum, predetermined thickness of paint or primer coating is applied and that a maximum, predetermined thickness of a paint or primer coating is not exceeded, it would be desirable to accurately nondestructively determine the thickness of a paint or primer coating on a surface. Currently known nondestructive measurement techniques are limited in their applicability.

In one known method, eddy current testing is used to determine paint thickness on metal substrates. As is known, eddy current testing detects electrical currents, known as eddy currents that propagate within the metal substrate. As a result, eddy current testing can only be used to determine thickness of paint or primer that is coated onto a surface of a metal substrate.

In another known method, ultrasound testing is used to determine thickness of a paint or primer coating on a surface of a composite or plastic substrate. However, ultrasound testing is not as reliable as eddy current testing, and also exhibits reduced accuracy for coating thickness below approximately 0.0002 inches (2 mils).

Near infrared (NIR) testing has been successfully used to measure paint and primer thickness on a variety of substrate materials. However, NIR methods to date have been more difficult for paint or primer thickness of less than 2 mils and for shiny coatings. At least part of the problem in obtaining accurate and reproducible thickness measurements is due to specular reflectance from the coating that interferes with the NIR diffuse reflectance spectra.

Therefore, there is an unmet need to provide a system and method to accurately and nondestructively measure paint thickness regardless of the substrate material on which the paint is coated, and to obtain accurate measurements for thin coatings, especially coatings of less than 2 mils thick, and for coatings that have shiny surfaces.

SUMMARY OF THE INVENTION

An accurate, nondestructive near infrared (NIR) system and method is provided to address the aforementioned and other disadvantages associated with prior NIR systems and methods for measuring paint thickness. In one embodiment of the invention, the system includes placing a diffuser between the coating and the NIR reflected light detector. In another aspect, the method includes transmitting NIR radiation towards a coated substrate and collecting the reflected NIR light that has passed through a diffuser.

To determine the coating thickness, the relative absorbance levels of the NIR light is determined and correlated to a coating thickness value. NIR light is directed at the coating and diffusely reflected NIR light is collected. Absorbance wavelengths having relatively high absorbance and relatively low absorbance are then identified and selected. The absorbance values at selected wavelengths are then correlated with known material thicknesses. The diffuser minimizes specular effects from the coating that causes interferences in the NIR spectra and allows for accurate determinations, especially for coating thicknesses below 2 mils and for coatings that have a shiny surface.

Systems to measure thin coating thickness by NIR measurement methods have been developed in U.S. Patent Publication Number 2005/0263704, filed May 16, 2005, and U.S. Pat. No. 6,903,339, filed Nov. 26, 2002, which are incorporated herein by reference. However, these systems are limited in their ability to accurately measure coating thickness below 2 mils and to accurately measure coating thickness when the coating has a shiny finish. By placing a diffuser between the coating surface and the reflected NIR light collector, an improvement has been made in accurately measuring coating thickness in both of these situations.

The diffuser improves the accuracy of NIR measurements by correcting for variations in the substrate surface and eliminating spurious variance due to specular light effects on the surface coatings. The diffuser eliminates serious interference effects in thin transparent coatings, which generally results in thickness determinations that are much more reproducible and accurate. In applications where the substrate surface is a composite, the diffuser compensates for variations due to graphite fiber orientation.

The invention provides a method for calibrating a NIR diffuse reflection probe, hereinafter referred to as a NIR probe, especially for coating calibration standards of less than 2 mils in thickness. The first step of the calibration method is to make a background reference for the NIR probe against a reflectance standard. A diffuser is placed between the reflectance standard the and light collector of the NIR diffuse reflection probe during the referencing of the probe. Then, the method includes placing the diffuser between a thin plastic thickness standard mounted upon the reference standard and the NIR light collector of the NIR probe to calibrate the probe. The reference standard may be formed of a biaxially-oriented polyethylene terephthalate (boPET) polyester film, such as Mylar produced by E.I. du Pont de Numours and Company, or any other suitable NIR calibration standard material. The NIR probe is then calibrated for a desired range of thickness standards. The diffuser may be used with a handheld NIR probe or other spectrometer for measuring coating thickness.

The diffuser is formed of a low density polytetrafluoroethylene (PTFE) fluoropolymer thin film, such as Teflon® made by E.I. du Pont de Numours and Company, that does not have NIR absorbance bands but scatters diffuse NIR light. The diffuser is placed between the measuring device and the coating to be measured. The PTFE flouoropolymer thin film is almost transparent to NIR light, with the pore size of the film able to scatter NIR light. Thus, NIR light that is already diffusely reflected, coming in from many angles, is not significantly affected by the film, but specular light, light coming in form one angle only, is scattered and thus specular reflectance light is removed. The diffuser may be applied on the surface of the coating or upon the surface of the collector of the NIR probe.

The invention further provides for a method of determining a coating thickness using a NIR probe and a diffuser. The NIR probe includes a NIR source and a reflected NIR light collector that may be provided in a handheld unit. The NIR probe handheld unit may include a tip that allows for directing a NIR light beam onto a coating and for collecting reflected NIR light from the coating. The calibration is performed by first bringing the tip of the NIR probe into physical contact with a diffuse reflectance reflectance standard with the diffuser in between. A measurement is taken that is used as the background reference for the NIR probe. Next, a thin plastic reference standard is placed upon the reflectance standard. The diffuser is then placed between the thin plastic reference standard and the NIR probe light collector. The reflectance standard, thin plastic reference standard, diffuser and NIR probe are all brought into physical contact and the NIR probe is used to measure the absorbance value of the thin plastic thickness standard. Thickness standards of about 0.20 to about 10.00 are used to provide a range of accurate coating thickness absorbance values. A regression is performed to calibrate the coating thickness to the absorbance values.

The diffuser is formed of a low density PTFE thin film of a thickness of about 3 mils to about 4 mils. The diffuser may be formed of Teflon® made by E.I. du Pont de Numours and Company that is porous to NIR light. The diffuser may be placed between the thin plastic standard and the NIR probe by applying the diffuser to the surface of the thin plastic reference standard. Alternatively, the diffuser may be applied directly upon the tip of the NIR probe in such a way that reflected NIR light passes through the diffuser before being collected by the NIR probe collector.

The diffuser minimizes specular reflectance effects in light scattering materials such as paint and primer. To obtain accurate and reproducible thickness measurements, especially of coatings of less than 2 mils thickness and/or with shiny surfaces, the diffuser improves the measurement of the diffuse reflected NIR light and minimizes specular reflectance from substrate irregularities and coating surface reflections, the specular reflections, negatively impact the thickness measurement. Specular reflectance, especially from substrate irregularities in composite substrates, is much more problematic in NIR thickness measurements for coatings that are less than 2 mils.

The method may then be used to measure the thickness of a paint or primer coating upon a substrate. The coating may be opaque or transparent. The coating may be a polyurethane-base paint. It is understood, however, that measurement of other coatings, such as other paints materials and primers, including epoxy primers, latex paint, enamel paint, filled stains and varnishes, and other like coatings, may also be made.

The coating may be formed of two or more layers of different coating materials. The NIR measurement method may be used to determine the overall coating thickness when the outer coating layer is opaque and less than about 5 mils thick. Also, the NIR measurement method may be used to determine the overall coating thickness when the outer coating is transparent and less than about 40 mils. The diffuser may be used in measuring layered coatings, and has shown good results in reducing specular reflectance, especially in shiny coating outer layers.

The substrate may be a composite. The substrate may be formed of various composite resins, thermoforming and thermosetting plastics, wood, fiberglass, and other similar materials, and are considered within the scope of the present invention.

Further aspects of the method and system are disclosed herein. The features as discussed above, as well as other features and advantages of the present invention will be appreciated and understood by those skilled in the art from the following detailed description and drawings.

DETAILED DESCRIPTION OF THE INVENTION

The present invention now will be described more fully hereinafter with reference to the accompanying drawing, in which a preferred embodiment of the invention is shown. This invention may, however, be embodied in many different forms and should not be construed as limited to the embodiments set forth herein; rather, these embodiments are provided so that this disclosure will be thorough and complete and will fully convey the scope of the invention to those skilled in the art.

Figure 1:
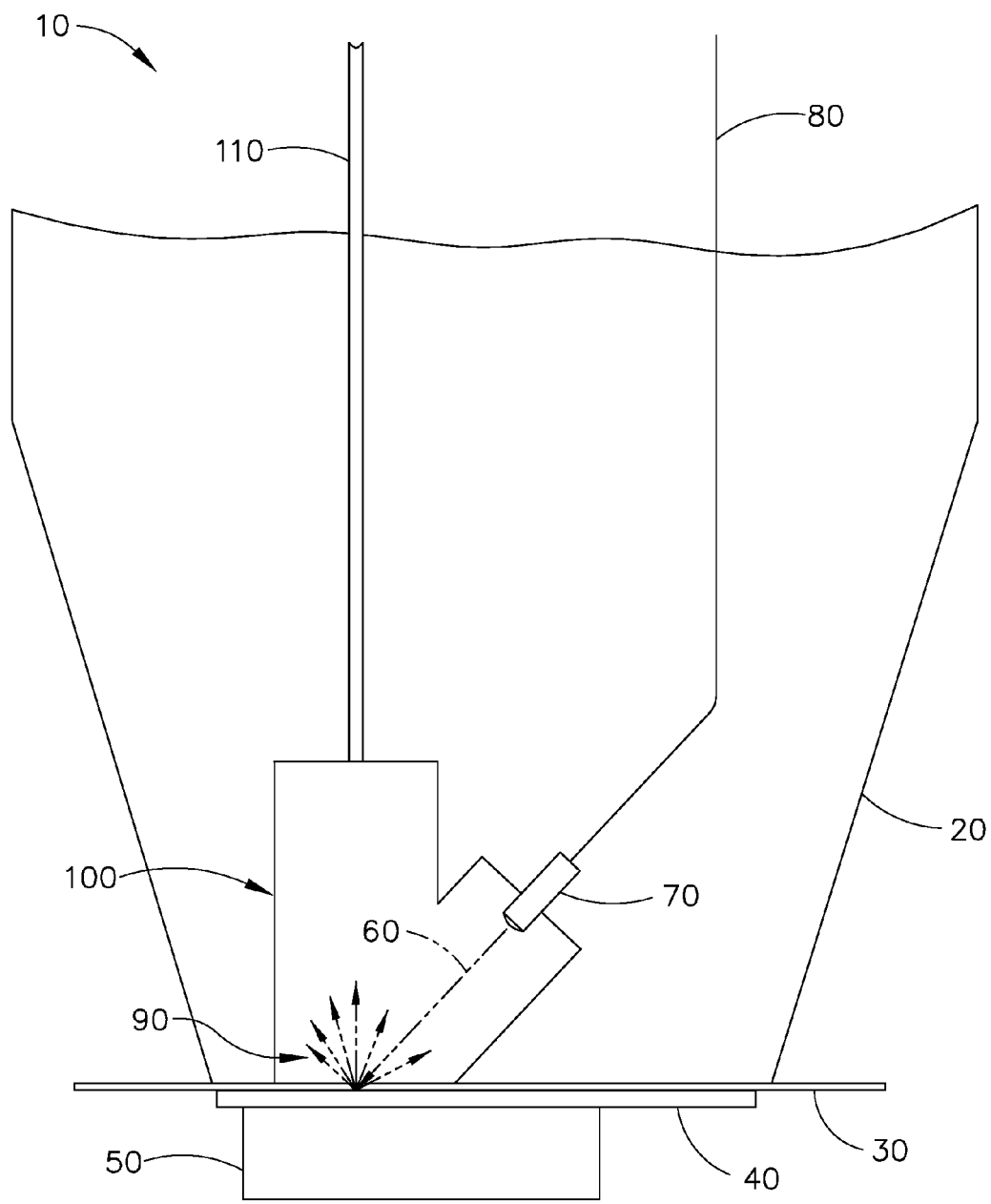
FIG. 1 shows an arrangement of an embodiment of the NIR thickness measurement system of the current invention during calibration

Referring to FIG. 1, there is illustrated an arrangement of the NIR thickness calibration measurement system 10 in accordance with a preferred embodiment of the present invention. The NIR thickness calibration measurement system 10 is formed of a NIR diffuse reflection probe 20, hereinafter referred to as a probe 20, a diffuser 30, a thickness standard 40, and a reflectance standard 50. The reflectance standard 50 is a diffuse reflectance standard.

The first step in calibrating the NIR coating thickness measurement system 10 is to reference the probe 20 with the reflectance standard 50 without the thickness standard 40 in place. The probe 20 is brought into contact with the diffuser 30 that is in contact with the reflectance standard 50 to reference the probe 20.

A NIR light beam 60 is directed upon the reflectance standard 50 from a NIR light beam source 70. The NIR light beam source 70 receives power from a light source power supply 80. The reflected NIR light 90 is collected by the NIR light collector 100 and fed via a fiber optic light pick-up 110 to a spectrometer (not shown) to determine the reflected NIR light reading. The reference spectrum of the reflected NIR light reading is is saved for later absorbance calculations.

Then, as shown in FIG. 1, a thickness standard 40 formed of a thin plastic material of a known thickness is placed upon the reflectance standard 50. The diffuser 30 is then placed upon the reference standard 40. The probe 20 is placed in contact with the diffuser 20, so that the reflectance standard 50, the thickness standard 40, the diffuser 30 and the probe 20 are all in sequential contact.

An NIR light beam 60 is directed upon the thickness standard 40 from a NIR light beam source 70. The NIR light beam source receives power from a light source power supply 80. The reflected NIR light 90 is collected by the NIR light collector 100 and fed via a fiber optic light pick-up 110 to a spectrometer (not shown) for measurement. An absorbance spectrum is then calculated as −log(thickness spectrum/reference spectrum).

The diffuser 20 may be a low density Teflon® thin film of a thickness of about 3 mils to about 4 mils. Commercially available Teflon® plumbers tape or a custom Teflon® sheet may be used for the diffuser.

The thickness standard 40 may be a calibrated Mylar® shim, or any other available reference standard suitable for NIR calibration. The reference standard 40 should be able to allow for calibration from about 0.20 to about 10.00 mils.

In another embodiment of the invention, the diffuser 30 is placed directly upon the probe 20 so as to diffuse reflected NIR light reaching a NIR light collector 100 of the probe 20 passes through the diffuser 30. The diffuser 30 may be attached by a housing or nose containing the diffuser directly to the probe 20.

In a second embodiment of the invention, the diffuser is used to improve the accuracy of a NIR coating thickness measurement system 200. The first step in measuring the thickness of a coating 210 is to provide a calibrated NIR diffuse reflection probe 20, hereinafter referred to as probe 20. The probe 20 may be calibrated by the method discussed above.

It is always necessary to use the standard single-beam spectroscopy method and collect a reference spectrum on the reflectance standard 50 and calculate the sample absorbance spectrum with the method −log(I/Io), where I is the sample spectrum and Io is the reference spectrum. A series of samples of known coating thickness as provided by the reference standard 40 are used to calibrate the size of the absorbance bands to the coating thickness of the samples.

Figure 2:
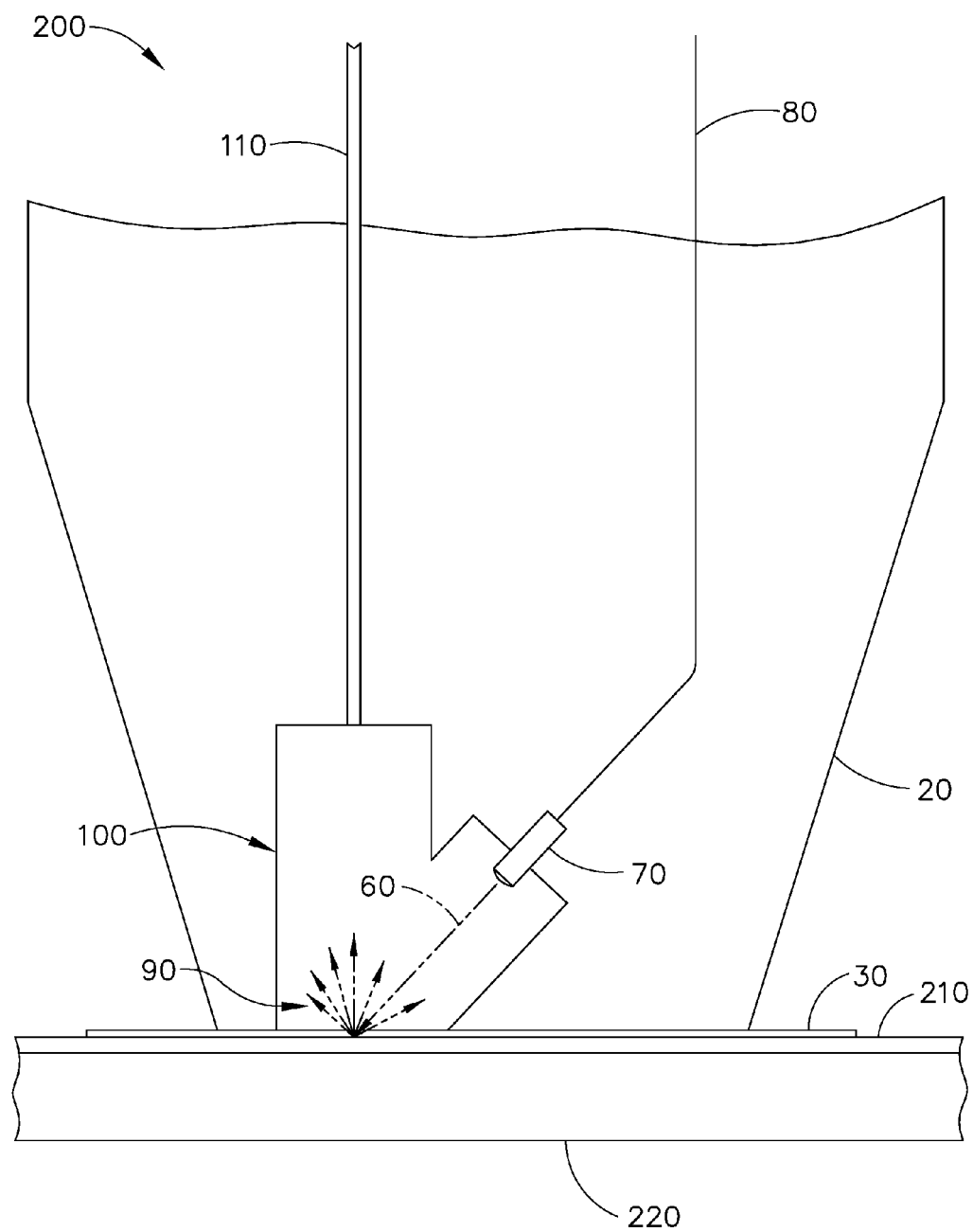
FIG. 2 shows an arrangement of an embodiment of the NIR thickness measurement system of the current invention during coating measurement.

Then, as shown in FIG. 2., a coating 210 upon a substrate 220 is provided. A diffuser 30 is placed between the coating 210 and the probe 20. AS shown in FIG. 2., the probe 20, the diffuser 30 and the coating 210 are brought into direct sequential contact.

An NIR light beam 60 is directed upon the coating 210 from a NIR light beam source 70. The NIR light beam source receives power from a light source power supply 80. The reflected NIR light 90 is collected by the NIR light collector 100 and fed via a fiber optic light pick-up 110 to a spectrometer (not shown) for measurement.

The diffuser 30 is a low density Teflon® film of a thickness of about 3 mils to about 4 mils. Commercially available Teflon plumbers tape or a custom Teflon sheet may be used for the diffuser. The diffuser 30 may be applied to the coating as shown in FIG. 2. Alternatively, the diffuser 30 may be attached to the probe 30 by a housing or nose containing the diffuser 30 directly to the probe 20.

The coating may be a primer or paint applied to a substrate. The coating may be opaque or transparent. The coating may be a polyurethane based paint. It is understood, however, that measurement of other coatings, such as other paints materials and primers, including epoxy primers, latex paint, enamel paint, filled stains and varnishes, and other like coatings, may also be made. The coating may be formed of layers of different coating materials. The NIR measurement technique will determine the overall thickness of the coating.

The NIR measurement method has been used to determine the total coating thickness of a two layer coating when the outer coating layer is opaque and less than about 5 mils thick. Also, the NIR measurement method has been used to determine the overall coating thickness of a two layer coating when the outer coating is transparent and less than about 40 mils. The diffuser has shown good results in reducing specular reflectance in two layer coatings, especially for two layer coatings when the outer layer has a shiny surface.

The substrate may be a metal or composite. The substrate may be formed of various composite resins, thermoforming and thermosetting plastics, wood, fiberglass, and other similar materials, and are considered within the scope of the present invention.

The NIR diffuse reflection probe was used to measure coating thickness from approximately 0.20 mils to approximately 10.00 mils and accurately measured coating thicknesses of a variety of coating materials as confirmed by destructive and other nondestructive techniques including ultrasonic and eddy current measurement.

It will be appreciated, however, that the present invention is not limited to the flat geometry of the coated surface, but that the principals and teachings as set forth herein could be used to produce a coating thickness measurement system capable of determining coating thickness upon a variety of substrate geometries.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A system for calibrating a NIR probe, consisting essentially of:
   a NIR probe comprising a NIR light collector;
   a thickness standard;
   a reflectance standard; and
   a diffuser consisting essentially of a low density polytetrafluoroethylene fluoropolymer thin film;
   wherein the NIR probe is first placed against the reflectance standard to reference the probe, and then placed against the thickness standard to calibrate the NIR probe; and
   wherein the diffuser is placed between the NIR light collector and the reflectance standard and between the NIR light collector and the thickness standard.

2. The system of claim 1, wherein the reference standard further comprises shims of between 0.20 and 10.00 mils thick.

3. A system of claim 1, wherein the low density polytetrafluoroethylene fluoropolymer thin film is between 3 mils and 4 mils thick.

4. A system for measuring a coating thickness, consisting essentially of:
- a calibrated NIR probe comprising a NIR light collector;
- a coating having a thickness upon a substrate; and
- a diffuser consisting essentially of a low density polytetrafluoroethylene fluoropolymer thin film;
- wherein the thickness of the coating is measured by placing the calibrated NIR probe against the coating with the diffuser placed between the coating and the NIR light collector to measure the thickness of the coating.

5. The system of claim 4, further comprising wherein thin film, low density polytetrafluoroethylene fluoropolymer is between 3 mils and 4 mils thick.

6. The system of claim 4, further comprising wherein the coating comprises a paint or a primer.

7. A NIR light diffuser consisting essentially of:
- a low density polytetrafluoroethylene fluoropolymer thin film; and
- a housing to attach the low density polytetrafluoroethylene fluoropolymer thin film to a NIR spectrometer.

8. A method for determining a coating thickness, consisting essentially of:
- providing a coated substrate comprising a coating having a thickness;
- directing a NIR light from a NIR light source at the coating;
- collecting reflected NIR light reflected from the coating by a NIR light collector; and
- determining the coating thickness from the collected reflected NIR light;
- wherein, a diffuser consisting essentially of a low density polytetrafluoroethylene fluoropolymer thin film is placed between the coating and the NIR light collector.

9. The method of claim 8, wherein the NIR light source and the NIR light collected are contained in a hand-held NIR diffuse reflection probe.

10. The method of claim 8, further comprising wherein the coating comprises a paint or primer.

11. The method of claim 8, further comprising wherein the substrate comprises a metal or a composite.

12. The method of claim 8, further comprising wherein the diffuser is attached to the NIR diffuse reflection probe.

13. A method of calibrating a NIR diffuse reflection probe, comprising:
- providing a NIR diffuse reflection probe comprising a NIR light collector;
- referencing the NIR diffuse reflection probe with a reflectance standard;
- placing a reference standard upon the reflectance standard;
- calibrating the NIR diffuse reflection probe against the reference standard;
- wherein a diffuser is placed between the NIR light collector and the reflectance standard during the referencing and the between the NIR light collector and the reference standard during the calibrating of the NIR diffuse reflection probe.

14. The method of claim 13, further comprising wherein the diffuser is a low density polytetrafluoroethylene fluoropolymer thin film.

15. The method of claim 13, further comprising wherein the NIR diffuse reflection probe is a hand-held unit.

16. The method of claim 13, wherein the diffuser is attached to the NIR diffuse reflection probe.

* * * * *